United States Patent [19]
Fargeas et al.

[11] Patent Number: 5,259,174
[45] Date of Patent: Nov. 9, 1993

[54] JAW FOR TRACTION TESTS ON TEST PIECE SLIVERS WITHOUT HEELS

[75] Inventors: Franck Fargeas, Audenge; Daniel Reyrau, Saint Medard en Jalles; Michel Cussac, La Teste; Marcel Bourely, Saint Aubin de Medoc, all of France

[73] Assignee: Aerospatiale Societe Nationale Industrielle, Paris, France

[21] Appl. No.: 774,508

[22] Filed: Oct. 10, 1991

[30] Foreign Application Priority Data

Oct. 11, 1990 [FR] France ................................ 90 12543

[51] Int. Cl.$^5$ .............................................. G01N 3/08
[52] U.S. Cl. .................................................... 73/833
[58] Field of Search ................ 73/831, 833, 856, 860; 269/271, 273–275, 279, 280

[56] References Cited

U.S. PATENT DOCUMENTS

| | | | |
|---|---|---|---|
| 525,243 | 8/1894 | Vare | 269/273 |
| 2,792,731 | 5/1957 | Turner | 269/279 |
| 2,796,787 | 6/1957 | Aske | 269/279 |
| 3,273,933 | 9/1966 | Jochim | 269/274 |

FOREIGN PATENT DOCUMENTS

| | | | |
|---|---|---|---|
| 341434 | 10/1921 | Fed. Rep. of Germany | 269/274 |
| 1139302 | 11/1962 | Fed. Rep. of Germany | |
| 8529717.8 | 3/1986 | Fed. Rep. of Germany | |
| 675344 | 7/1979 | U.S.S.R. | |

*Primary Examiner*—Robert Raevis
*Attorney, Agent, or Firm*—Nikaido, Marmelstein, Murray & Oram

[57] ABSTRACT

The linings of a jaw for traction tests on test piece slivers are made of a moulded material having evolutive hardness and shearing modulus with a variable thickness according to the height of the jaw so as to distribute the clamping forces over this height. This distribution of forces is completed via an excentration of the point of application of the clamping force. Traction tests are performed on test piece.

8 Claims, 1 Drawing Sheet

JAW FOR TRACTION TESTS ON TEST PIECE SLIVERS WITHOUT HEELS

FIELD OF THE INVENTION

The invention, which relates to the technical field of devices for testing and assessing the mechanical characteristics of composite materials, more particularly concerns a special jaw making it possible to maintain test piece slivers without heels for traction tests.

BACKGROUND OF THE INVENTION

Test pieces embodied from staple slivers impregnated with martrices are used in many ways for traction tests. Up until now, traction tests are carried out by traction machines using clamping jaws controlled, for example, by a pneumatic, hydraulic or self-clamping system on test piece slivers without heels whose production proves to be long and costly. In fact, as regards resin matrices, these slivers are manufactured in a machine impregnated with resin from a coil of dry fiber made, for example, of carbon, glass or silicon. The percentage of impregnation of the sliver may be adjusted by a pulley system and the sliver is then wound onto a mandrel and polymerized at 60° C. in an oven. Then, after the sliver is polymerized, carbon or metal heels intended to prevent the sliver from sliding are conventionally glued on the test piece. The production cost of these test pieces is obviously high, and embodying the heels alone is relatively expensive. Apart from this drawback, so as to test the heels, the glue on the heels must first be dried, which may delay the test by 24 hours. On the other hand, this technique no longer allows the test to continue until the new carbon fibers with improved mechanical characteristics are ruptured.

This is why orientation is moving towards the embodiment of test piece sliver without heels, which reduces their cost price and allows time to be saved on conducting tests.

However, with test piece slivers without heels, new difficulties arise due to the fact that sliding of the sliver in the clamping jaw needs be avoided during traction test, in particular, as regards the considerable stresses attained with the use of carbon slivers.

A certain number of techniques are used to prevent the slivers from sliding. For example, self-clamping conical and ribbed jaws are used on currently-used traction machines. If clamping has the effect of increasing the forces on the test piece during traction, it does not eliminate concentration of the force at the jaw outlet. Apart from other test pieces, this is suitable for metallic test pieces. Secondly, they act on the surface of the test piece and create clamping stresses not compatible with test piece slivers without heels. There also exists the technique consisting of coating the clamping jaw with abrasive papers to avoid sliding. But it has been observed that this would involve rapid wear of the abrasive paper and a large consumption of slivers due to the fact that frequently the grain of the paper is too aggressive for the filaments of slivers and causes them to rupture in the jaw. It thus follows that, in order to obtain a value with a small standard difference, it is necessary to break more slivers two or three times during the tests.

Finally, there currently exists a technique consisting of coating the clamping jaws with elastomers. This has the advantage of protecting the sliver when the gripping jaws are reclosed along the sliver. Thus, when the jaws close under the force of the closing pressure, the elastomer imprisons the test piece and thus prevents sliding. Nevertheless, the level of force remains insufficient when this involves testing highly resistant slivers or slivers with a large section. In this case, there is sliding in the jaws or shearing ruptures the elastomer or, when the clamping pressure is increased, the sliver breaks when flush with the jaw. In fact, the traction force in the sliver moves by shearing stresses to the interface between the jaw and the sliver whose field is considerably non-linear. Thus, it is possible to increase the length of the jaws or their clamping force, although the problem would nevertheless be resolved with ruptures still occurring at the outlet of the jaws. In order to avoid this happening, it has been considered using non-conical clamping jaws nesting inside each other, these jaws extending over a certain height so as to be able to take up the traction forces by means of shearing of the soft material mounted on the jaws. But in this case, the operation for placing and removal of the sliver proves to be long and difficult; in addition, the change of internal coatings of the jaws proves to be delicate and requires that the tests be halted for several days. In short, it can be seen that rupture flush with the jaws results in several stresses being superimposed, namely a traction stress distributed in the sliver, a compression stress introduced by the jaws and a shearing stress resulting from the force introduction mode.

SUMMARY OF THE INVENTION

The object of the invention is to resolve all these drawbacks by virtue of proposing traction machine jaw linings for tests with test piece slivers without heels whose mechanical behaviour makes it possible to test slivers with extremely high rupture stresses and thus render them applicable for tests of large section slivers made of materials with high-performance characteristics using carbon fibers, for example. These new jaws make it possible to progressively introduce shearing forces along the test piece-jaws interface so as to avoid damaging the sliver or break it when flush with the jaws, while at the same time being relatively easy to implement.

The main object of the present invention thus consists of one jaw for traction tests on test piece slivers without heels, said jaw comprising linings made of a soft material with evolutive hardness and a modulus of elasticity and of variable thickness according to the height of the jaw so as to distribute the clamping forces over this height, this distribution of forces being able to be completed via an excentration of the point of application of the clamping force.

More specifically, the linings have a thickness measured at one extremity of the jaws on the side of the end of the sliver, this thickness being smaller than its thickness measured at its opposing extremity, and said linings are moulded on profiled soles embodying the interface with the base of the jaws and compensate for the variable thickness of the linings.

According to one main characteristic of the invention, the linings are made of a non-homogeneous material over their entire height so that their hardness and modulus of elasticity are larger in the portion with the larger thickness than in the portion with the smaller thickness, and advantageously the material of the linings is made of epoxy resin progessively charged with pyrex powder from one extremity to the other.

The object of the invention is also to provide a method to embody the moulded evolutive hardness linings of the jaw according to which polymerization is effected of the resin and its charge constituting the lining by slanting the production mould so as to provoke via decantation a modulated charge accumulation towards the extremity of the lining.

BRIEF DESCRIPTION OF THE DRAWINGS

The particular characteristics and advantages of the invention shall appear more readily from a reading of the following description of one embodiment with reference to the accompanying drawings on which.

DETAILED DESCRIPTION OF THE DRAWINGS

Figure 1:
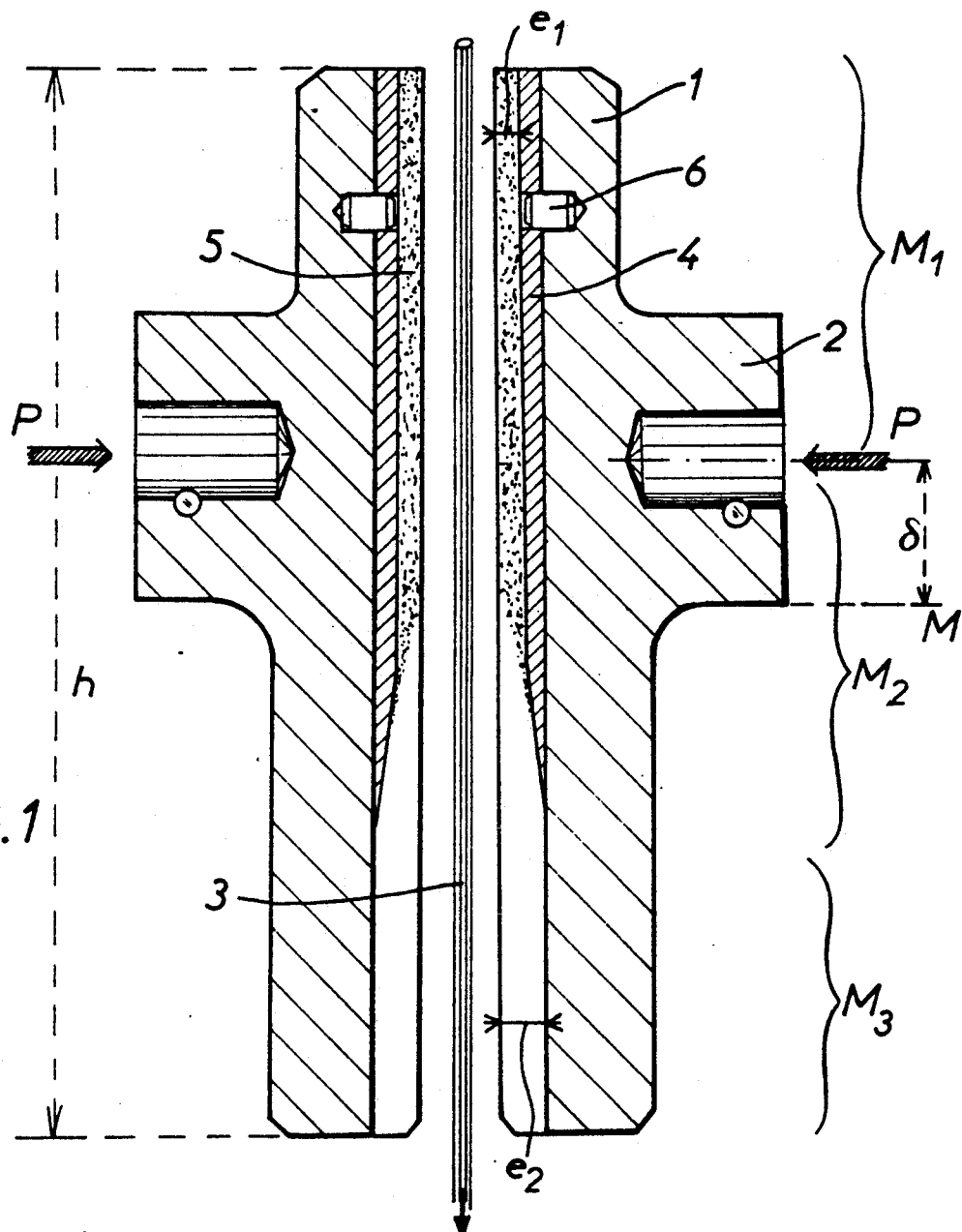
FIG. 1 is a diagrammatic cutaway view of a clamping jaw of a test piece sliver without heels.

The clamping jaw 1 used has the general structure shown on FIG. 1. It extends over a height h on both sides of a median horizontal axis M. Each of the two lateral portions of the jaw is subjected to a clamping force P, not exerted at its center but on heels 2 excentrated by a value δ with respect to the axis M. The pressure force is thus applied to a central sliver 3, this force being greater towards the upper free extremity of the sliver than at the other side. The jaw is equipped with slugs 6 for internally fixing a sole 4 bearing linings 5. The figure shows that the linings have a particular irregular profile. In fact, their thickness e1 measured at the top portion of the jaw is much smaller than the thickness e2 measured at the base. This upper portion of the jaw where the thickness e1 is measured corresponds to the portion enclosing the end of the sliver 3, whereas the bottom portion corresponds to the other extremity of the jaw from which the sliver comes out in the direction of the opposing jaw. The linings 5 are advantageously directly moulded on the soles 4 made, for example, of aluminium, the aim of the latter being to embody the interface with the base of the jaws but also to compensate for the variable thickness of the linings. The soles are thus tapered and have a flared profile whose advantages are to be described subsequently. The linings 5 are kept by a double-sided adhesive on the soles and the jaws in a vertical position when the jaws are open. The slugs 6 make it possible to position the grips in the clamping jaws, which favors a rapid quality change of the linings.

Linings 5 thus have a variable thickness, but are also made of a non-homogeneous material over their entire height, in other words the constitutive material is more charged in the upper portion with the smaller thickness, as shown by the small points visible on FIG. 1. Thus, the material in the linings is made, for example, of epoxy resin progressively charged with pyrex powder from one extremity to the other. The hardness of the lining is thus greater in the small thickness portion e1 than in the large thickness portion e2. The lining is polymerized, that is the resin and its charge, by slanting the production mould by about 12 degrees, which has the result of provoking via decantation a modulated charge accumulation towards the extremity of the lining. This ideal inclination of 12 degrees makes it possible to obtain a tangential evolution between the greater hardness charged portion and the smaller hardness non-charged portion and allows for the pyrex powder to migrate towards the bottom of the mould in the resin.

It shall be observed that the clamping jaw previously described thus uses a moulded lining with a variable thickness (evolving from e1 to e2) and which has an evolutive modulus of elasticity and hardness between its thick portion and the thinner portion. In addition, the clamping force of the jaw is distributed from the off-center point of application.

By virtue of the above, there is therefore an evolution of the clamping force along the grip of the jaw, constituted by the lining 5 and the sole 4.

In the upper zone M1, that is the zone where the lining 5 is charged and where application of the force P is the greatest owing to its excentration, the sliver 3 shall be strongly clamped, thus enabling an equally high traction force to be exerted on the latter in the direction indicated by the arrow and introduces a large part of the shearing force in one zone of the test piece so as to tensile-stress the latter. Any possible deterioration of the upper extremity portion of the sliver does not constitute any particular drawback. In the intermediate zone M2, the widening out of the lining towards a thicker zone with reduced hardness shall allow for a certain deformation under the force and enable said lining to notch the shape of the sliver and increase the contact surface. Instead of one punctual clamping surface, a tangential clamping point is obtained by flaring, as well as a distribution of the clamping forces along the sliver, this distribution evolving in an increasing way.

Finally, the lower zone M3 of the lining is flexible so as to avoid damaging the sliver test piece and avoid any rupture of the sliver when flush with the jaws at a level where the sliver is already considerably stressed and where any excess stress would generate a rupture. It is essential that this rupture zone does not occur inside the jaws or flush with the jaws so as to be freed of any uncertainty linked to any clamping disturbances, clamping providing a field of non-homogeneous stresses. The shearing module of the material of the lining is larger in the thin sliver portion (zone M1) than in the thicker portion, the shearing deformation of the slivers being much smaller towards the free portion of the sliver, which contributes in further charging the extremity of the sliver.

Figure 2:
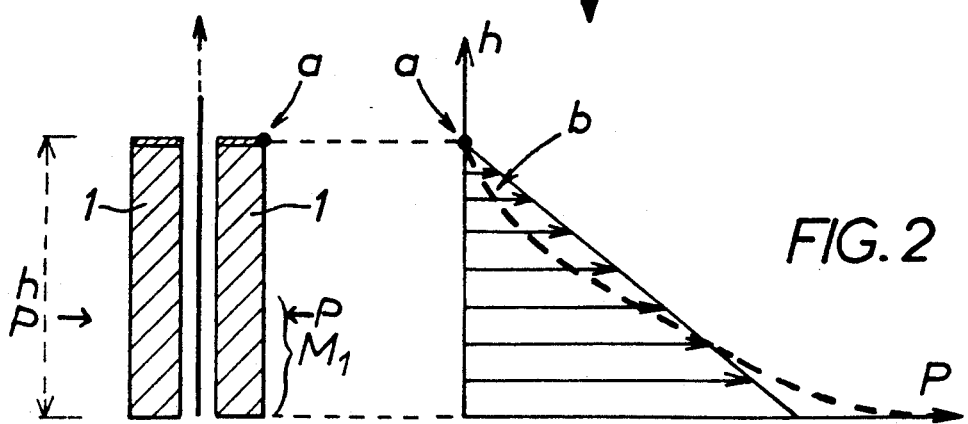
FIG. 2 is a curve showing the evolution of the pressure force.

This evolution of the clamping force along the gripper of the jaw, that is its lining and the sole, is shown on FIG. 2. This figure diagrammatizes the jaw 1 with a height h subjected to application of the clamping forces P. It can be seen on the adjacent curve that the pressure force is greater in the zone M1 on the side of the sliver extremity, that is at the location where the traction stress is lowest. This theoretical representation shows the singular point corresponding to the zone where the sliver breaks. Thus, the punctual force is attenuated or even suppressed at the point a on the sliver via a widening out b of the curve corresponding to a tangential clamping of the sliver, as indicated earlier.

The jaw described above is thus "evolutive" since, according to its height, there is an evolution of the clamping force, evolution of the thickness of the lining and an evolution of the shearing module of the interface.

What is claimed is:

1. Jaw for traction tests on test piece slivers without heels, said jaw comprises:
  a jaw body;

linings coupled to said jaw body which have a variable thickness according to a height of the jaw body, wherein the linings also have an evolutive modulus of elasticity and hardness according to the height of the jaw body so as to distribute clamping forces over said height and wherein the clamping forces are distributed by an off-center point of application of the clamping force.

2. Jaw according to claim 1, wherein the linings are molded onto profiled soles embodying the interface with a base of the jaw body and correspond to the variable thickness of the linings.

3. Jaw according to claim 2, wherein the linings are fastened to the soles and the jaw body by double-sided adhesive.

4. Jaw according to claim 2, wherein slugs are provided for fastening soles on internal walls of the jaw body.

5. Jaw according to claim 1, wherein the linings are made of a non-homogeneous material over an entire height thereof so that the hardness and modulus of elasticity thereof are greater in a thinner portion than in a thicker portion.

6. Jaw according to claim 5, wherein the linings comprise epoxy resin more charged with pyrex powder in a high part of small thickness than in a low part.

7. Jaw according to claim 1, wherein the clamping force of the jaws is exerted at an off-center point with respect to a horizontal median axis, said off-center point being closer to a free extremity of the sliver.

8. Jaw according to claim 1, 2 or 7, wherein, in an intermediate zone of the jaw, the linings are widened out between thinner and thicker zones so as to increase a contact surface and so that distribution of forces along the sliver evolves increasingly.

* * * * *